United States Patent
Egorov et al.

(10) Patent No.: US 8,361,993 B2
(45) Date of Patent: Jan. 29, 2013

(54) HYDROXY-BISPHOSPHONIC ACID DERIVATIVES AS VECTOR TARGETING BONE TISSUE

(75) Inventors: Maxim Egorov, Nantes (FR); Yannick Fortun, Mauves sur Loire (FR); Dominique Heymann, Indre (FR); Jacques Lebreton, Nantes (FR); Monique Mathe, Nantes (FR); Marc Padrines, Carquefou (FR); Francoise Redini, Sautron (FR)

(73) Assignees: Universite de Nantes, Nantes (FR); Institut National de la Sante et de la Recherche Medicale (INSERM), Paris (FR); Centre National de la Recherche Scientifique (CNRS), Paris (FR)

( * ) Notice: Subject to any disclaimer, the term of this patent is extended or adjusted under 35 U.S.C. 154(b) by 262 days.

(21) Appl. No.: 12/811,602

(22) PCT Filed: Jan. 5, 2009

(86) PCT No.: PCT/EP2009/050027
§ 371 (c)(1),
(2), (4) Date: Jul. 2, 2010

(87) PCT Pub. No.: WO2009/083614
PCT Pub. Date: Jul. 9, 2009

(65) Prior Publication Data
US 2010/0311695 A1 Dec. 9, 2010

(30) Foreign Application Priority Data
Jan. 3, 2008 (FR) ...................................... 08 50021

(51) Int. Cl.
*A01N 57/00* (2006.01)
*A61K 31/66* (2006.01)
*C07F 9/02* (2006.01)
*C07F 9/28* (2006.01)

(52) U.S. Cl. ................................ 514/114; 564/15; 568/8

(58) Field of Classification Search .................. 514/114; 564/15; 568/8
See application file for complete search history.

(56) References Cited

U.S. PATENT DOCUMENTS
5,036,058 A 7/1991 Jaeggi
5,110,807 A 5/1992 Jaeggi

FOREIGN PATENT DOCUMENTS
DE 4011777 A1 10/1990
EP 0 387 194 A 9/1990
WO WO 97/12619 A1 4/1997
WO WO 02/062398 A2 8/2002

OTHER PUBLICATIONS

International Search Report issued for application No. PCT/EP2009/50027 on May 6, 2009.
Heymann et al., "Bisphosphonates: new therapeutic agents for the treatment of bone tumors," Trends in Molecular Medicine, vol. 10, No. 7, pp. 337-343, Jul. 2004.
Manolagas, "Birth and Death of Bone Cells: Basic Regulatory Mechanisms and Implications for the Pathogenesis and Treatment of Osteoporosis," Endocr. Rev., vol. 21, pp. 115-137, 2000.
Owen et al., "New Developments in Bone Formation," Current Opinion in Nephrology and Hypertension, vol. 7, pp. 363-366, 1998.
Roodman, "Advances in Bone Biology: The Osteoclast," Endocr. Rev., vol. 17, pp. 308-322, 1996.

*Primary Examiner* — Sreeni Padmanabhan
*Assistant Examiner* — Sarah Pihonak
(74) *Attorney, Agent, or Firm* — Foley & Lardner LLP

(57) ABSTRACT

The present invention relates to hydroxy-bisphosphonic acid derivatives corresponding to general formula (I): in which: -n and m denote, independently of one another, an integer ranging from 1 to 4, —X denotes an oxygen atom or an N—R3 group, —R1 and R3 denote, independently of one another, a linear or branched $C_1$ to $C_6$ alkyl group, and —R2 denotes a residue of a molecule of therapeutic or diagnostic interest, or pharmaceutically acceptable salts of said derivatives, and also the method for the preparation thereof and the therapeutic or diagnostic use thereof.

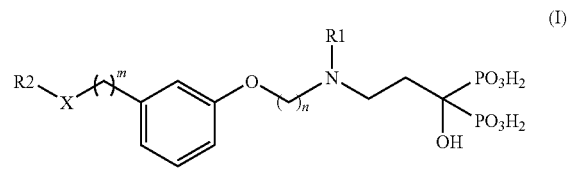

14 Claims, 4 Drawing Sheets

Control          Molecule (IV)

HYDROXY-BISPHOSPHONIC ACID DERIVATIVES AS VECTOR TARGETING BONE TISSUE

The present invention relates to novel hydroxy-bisphosphonic acid derivatives and to their use as a vector targeting bone tissue.

Bone tissue is connective tissue consisting of a mineral fraction consisting of calcium phosphate in the form of hydroxyapatite ($Ca_{10}(PO_4)_6(OH)_2$) crystals and of an organic fraction containing an extracellular matrix and specialized cells.

Bone tissue is perpetually being re-organized by means of a process called bone remodeling. It is characterized by an apposition phase due to the activity of osteoblasts which synthesize a new organic matrix and induce its mineralization (Owen et al., *Curr. Opin. Nephrol. Hypertens.* 1998, 7, 363) and a degradation phase provided by osteoclasts which resorb the organic matrix and dissolve the mineral portion (Roodman et al., *Endocr. Rev.* 1996, 17, 308). This physiological process allows to maintain the phosphocalcium homeostasis and the bone mass (Manologas et al., *Endocrin. Rev.* 2000, 21, 115) and to adapt to mechanical stresses. Any disturbance of this equilibrium is related to the occurrence of osteocondensing pathologies, such as osteopetrosis, or, most frequently, osteolytic pathologies which may be of tumoral origin (with primary tumors, such as osteosarcoma, or secondary tumors, such as bone metastases) or not in the case of metabolic pathologies such as osteoporosis.

Bisphosphonates (a basic form of bisphosphonic acid derivatives, to which belong hydroxy-bisphosphonic derivatives) are synthetic analogs of endogenous pyrophosphates for which the P—O—P chain has been replaced with a P—C—P chain, leading to metabolically stable compounds which represent an effective therapeutic tool of osteolyses (Heymann et al., *Trends Mol. Med.,* 2004, 10, 337).

These molecules were first of all used for their capability of targeting bone tissue. In the same way as pyrophosphates, bisphosphonates have strong affinity for the mineral portion of the bone (affinity between the phosphate groups and the calcium of the mineral portion of the bone) and may modulate at a strong dose the calcification process. The benefit of such substances has been demonstrated for treating various malfunctions of the bone metabolism. Bisphosphonates are in particular used for treating pathologies involving excessive bone resorption leading to hypercalcemia on the one hand and to bone affections at the origin of pains and fractures on the other hand.

Thus, their use has become essential since about ten years for treating osteoporosis, hypercalcemia of tumoral origin or not, as well as for tumoral osteolytic pathologies such as multiple myeloma or secondary bone metastases of a prostate or mammary carcinoma.

Structure-activity studies, developed to this day, have clearly shown that the capability of bisphosphonates for inhibiting bone resorption depended on two structural factors:
- the phosphonate groups (and hydroxy groups in the case of hydroxy-bisphosphoates), essential for good affinity of the compound with the mineral portion of the bone,
- the side chain R, specific to a molecular target, which determines the biological activity associated with the molecule.

hydroxy-bisphosphonate derivative:

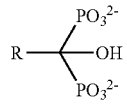

The present invention therefore relates to novel derivatives of hydroxy-bisphosphonic acid fitting the following general formula (I):

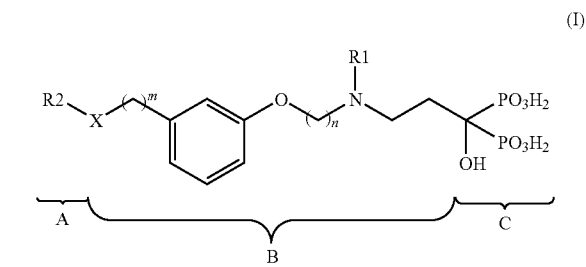

wherein:
- n and m designate, independently of each other, an integer varying from 1 to 4,
- X designates an oxygen atom or a N—R3 group,
- R1 and R3 designate, independently of each other, a linear or branched $C_1$-$C_6$ alkyl group and
- R2 designates a residue of a molecule of therapeutic or diagnostic interest, or pharmaceutically acceptable salts thereof.

The molecules of the invention therefore consist of three distinct portions:
- a portion C corresponding to the hydroxy-bisphosphonic acid function which will allow the molecule to target the bone tissue because of the strong affinity of this function for the mineral portion of the bone,
- a portion B which is a spacer arm, on which the residue R2 may be grafted, and finally
- a portion A corresponding to the residue R2 of a molecule with therapeutic or diagnostic activity, notably allowing targeted treatment of a pathology of the bone tissue or further diagnosis notably by imaging of this bone tissue.

By <<residue of a molecule of therapeutic or diagnostic interest>>, is meant, in the sense of the present invention, that a molecule of therapeutic or diagnostic interest is grafted on the spacer arm. Thus, the molecule of therapeutic or diagnostic interest should comprise a functional group allowing coupling with the spacer arm, i.e. coupling with a XH group (either —OH or —NHR3). Preferably, this functional group will be selected from a halogen atom or a —Z(O)R4 group with Z representing C, PR5 or SO; R4 representing a halogen atom or an OH, $N_3$ or OC(O)R6 group; R5 representing a hydrogen atom or an OR7 or R7 group; R6 representing a linear or branched $C_1$-$C_6$ alkyl group; and R7 representing a hydrogen atom or a linear or branched $C_1$-$C_6$ alkyl group. This functional group may also be selected from functions with acidity character (phenol, sulfonamide, succinimide and analogs), electrophilic functions [iso(thio)cyanates, aldehydes or further ketones], or further acceptor systems of the Michael type such as acrylates.

By acting on the length of the spacer arm, in particular by acting on the values of m and n, it will then be possible to promote rapid release of the active portion of the molecule (residue R2) or on the contrary ensure persistence of this active portion in order to allow extended delivery of the active ingredient or to carry out a diagnosis.

On the other hand, depending on the functional group of the molecule of therapeutic or diagnostic interest used for carrying out coupling with the spacer arm, stable bonds may be obtained between the portion A and the remainder of the molecule, which may be particularly interesting within the scope of molecules intended for diagnosis. In this case, the functional group may advantageously be selected from functions with acidity character, electrophilic functions and Michael acceptor systems, as defined earlier.

By <<alkyl>> group, is meant a linear or branched saturated hydrocarbon chain, including 1-6 carbon atoms, such as for example a methyl, ethyl, isopropyl, tertio-butyl, pentyl group, etc.

By <<halogen atom>> is meant a fluorine, bromine, chlorine or iodine atom.

By <<pharmaceutically acceptable salt>> is notably meant a salt obtained from pharmaceutically acceptable acids or bases.

Among pharmaceutically acceptable acids, mention may be made, in a non-limiting way, of inorganic acids, such as halohydric acids, such as hydrochloric and bromohydric acids, sulfuric, nitric or further phosphoric acids, or organic acids, such as acetic, propionic, benzoic, lactic, pyruvic, oxalic, malonic, succinic, maleic, fumaric, malic, tartaric, citric, mandelic, methanesulfonic, p-toluenesulfonic, cyclamic, salicylic, aspartic, stearic or further palmitic acids.

calcium metabolism, such as hypercalcemia, osteoporosis, and inflammatory pathologies, such as rheumatoid arthritis or peri-prosthetic loosenings.

In particular, the residue R2 may be selected from residues of active ingredient selected from standard chemotherapy agents, such as ifosfamide, derivatives of cis-platinum or doxorubicin, anti-inflammatory agents, such as cortico-steroids such as dexamethasone or non-steroidal anti-inflammatory agents like ibuprofen or indometacin, and peptides with bone pro-formation or anti-resorption activity.

The residue R2 may in particular originate from a molecule of therapeutic interest selected from alkylating anti-cancer molecules such as analogs of mustard gas; antineoplasic molecules such as doxorubicin, cis-platinum, adriamycin, actinomycin, fluorouracil, methotrexate, etoposide, vincristine, busulphan, docetaxel, 5-fluoro-uracil and their derivatives; anti-inflammatory agents such as ibuprofen, indometacin, bindazac, etodolic acid, lonazolac, and their derivatives; steroids such as derivatives of estradiol, estrone and dexamethasone.

The residue R2 may also originate from a molecule of diagnostic interest selected from fluorescein, fluorescein isothiocyanate (FITC), cyanin derivatives such as fluorescyanins and gallocyanin, alkaline or alkaline-earth sulfides and dansyl.

An example of a hydroxy-bisphosphonic acid derivative of the invention, more particularly intended for diagnostic use, thus fits the following formula (II):

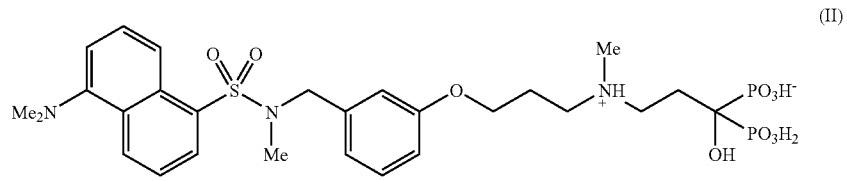

(II)

Among pharmaceutically acceptable bases, mention may be made, in a non-limiting way, of inorganic bases forming, for example, ammonium salts or salts of alkaline or alkaline-earth metals such as lithium, sodium, potassium, magnesium or further calcium, or organic bases such as triethylamine, diisopropylamine, piperidine, or further morpholine.

Advantageously, R1 will represent a methyl group. Also, when the group R3 is present, the latter will in particular represent a methyl group.

n may represent 1, 2, 3 or 4, and in particular 3.

In particular, the residue R2 of hydroxy-bisphosphonic acid derivatives of the invention may be selected from residues of fluorescent molecules, such as the (5-dimethylamino) naphthalene-1-sulfonyl (dansyl group) residue, the 7-nitro-1,2,3-benzoxadiazole (NBD group) residue or fluorescein, or further luminescent molecules, such as dioxetane derivatives. The corresponding hydroxy-bisphosphonic acid derivatives may then be used for imaging of the bone tissue, notably for diagnostic purposes.

Also, the residue R2 may be a residue of a useful active ingredient for treatment or diagnosis of a pathology of osteolytic or osteocondensing bone remodeling, such as primitive bone tumors (such as an osteosarcoma, a chondrosarcoma), a giant cell tumor or Ewing's sarcoma, bone metastases, multiple myeloma, deregulations of the phosphoformula which corresponds to the previous formula (I) for which:

n=3, m=1,

X=NMe,

R1=Me and

R2=

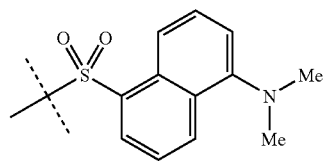

(dansyl group for fluorescence).

Examples of hydroxy-bisphosphonic acid derivatives of the invention, more particularly intended for therapeutic use, are the following:

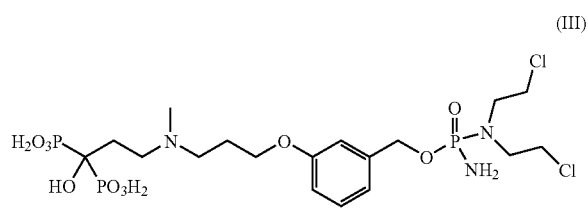

(potentially alkylating anti-tumoral molecule: contemplated applications to malignant hypercalcemia, primitive bone tumors and bone metastases),

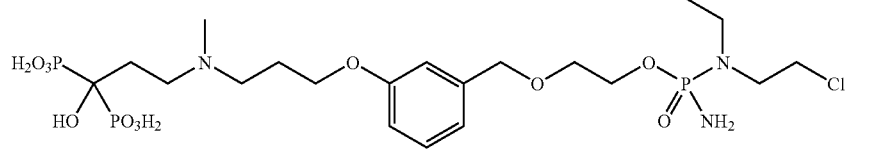

(potentially alkylating anti-tumoral molecule: contemplated applications to malignant hypercalcemia, primitive bone tumors and bone metastases),

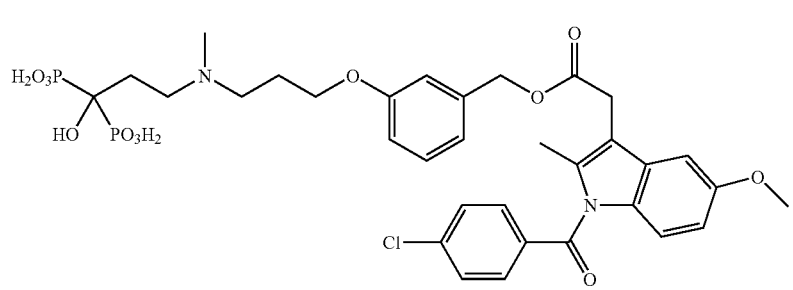

[molecule with anti-inflammatory function; application: rheumatoid arthritis; prepared from indometacin (non-steroidal anti-inflammatory agent, NSAI)], and

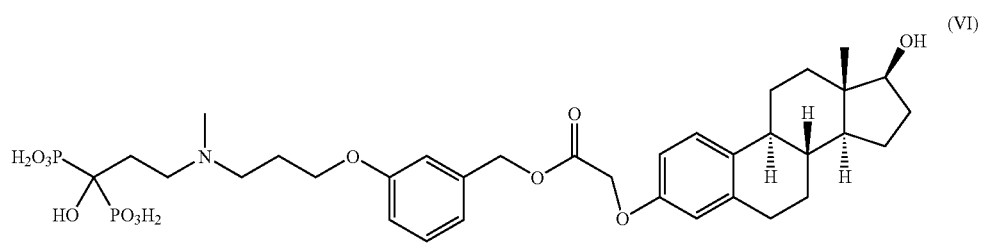

(molecule with hormonal/estrogenic function; application: osteoporosis; prepared from an estradiol derivative).

The present invention also relates to a derivative of hydroxy-bisphosphonic acid as described above or of a pharmaceutically acceptable salt thereof, for its use as a drug or as a diagnostic product, notably intended to target bone tissue.

The present invention also relates to the use of a hydroxy-bisphosphonic acid derivative of the invention or of a pharmaceutically acceptable salt thereof, for preparing a pharmaceutical or diagnostic composition targeting bone tissue.

In particular, the hydroxy-bisphosphonic acid derivatives of the invention may be used for imaging of bone tissue or for treating or diagnosing a pathology of osteolytic or osteocondensing bone remodeling, such as primitive bone tumors (such as an osteosarcoma, a chondrosarcoma, a giant cell tumor or Ewing's sarcoma), bone metastases, multiple myeloma, deregulations of the phospho-calcium metabolism, such as hypercalcemia, osteoporosis, and inflammatory pathologies, such as rheumatoid arthritis or peri-prosthetic loosenings.

According to a first embodiment, the hydroxy-bisphosphonic acid derivatives will be used for imaging the bone tissue.

According to a second embodiment, the hydroxy-bisphosphonic acid derivatives will be used in an anti-tumoral treatment, notably for treating malignant hypercalcemia, primitive bone tumors and bone metastases.

According to a third embodiment, the hydroxy-bisphosphonic acid derivatives will be used in the treatment of osteoporosis or in an anti-inflammatory treatment, notably for treating rheumatoid arthritis.

In a particular embodiment, m=1 and X=O will be selected for ensuring the release of the R2 radical and for allowing its action on the bone tissue.

In another particular embodiment, $m \geq 2$ will be selected in order to ensure persistence of the R2 radical, the latter then being attached in a more stable way onto the remainder of the molecule, thereby allowing possible use in imaging of bone tissue.

The present invention moreover relates to a pharmaceutical or diagnostic composition comprising at least one hydroxy-bisphosphonic acid derivative of the invention, as described earlier, or a pharmaceutically acceptable salt thereof and at least one pharmaceutically acceptable carrier.

This composition may be formulated so as to allow its administration notably via a sub-cutaneous, intravenous, oral, intramuscular or transdermal route, i.e. preferably as an injectable solution or as a patch.

The object of the present invention is also a pharmaceutical or diagnostic composition as defined above for its use as a drug or diagnostic product.

In particular, the compositions of the invention may be used for imaging of bone tissue or for treating or diagnosing a pathology of osteolytic or osteocondensing bone remodeling, such as primitive bone tumors, such as an osteosarcoma, a chondrosarcoma, a giant cell tumor or Ewing's sarcoma, bone metastases, multiple myeloma, deregulation of the phospho-calcium metabolism, such as hypercalcemia, osteoporosis and inflammatory pathologies, such as rheumatoid arthritis or peri-prosthetic loosenings.

According to a first embodiment, the diagnostic compositions will be used for imaging bone tissue.

According to a second embodiment, the therapeutic compositions will be used in anti-tumoral treatment, notably for treating malignant hypercalcemia, primitive bone tumors and bone metastases.

According to a third embodiment, the therapeutic compositions will be used in the treatment of osteoporosis or in an anti-inflammatory treatment, notably for treating rheumatoid arthritis.

The compounds of the invention may be prepared according to the following successive steps:

(a) coupling between a compound of the following formula (A):

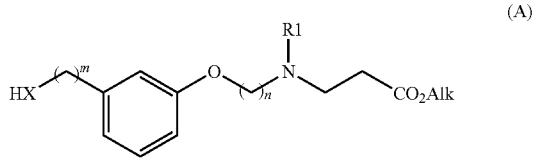

for which R1, X, N and m are as defined above and Alk represents a linear or branched $C_1$-$C_6$ alkyl group, and in particular a tert-butyl group,
and the molecule of therapeutic or diagnostic interest corresponding to the residue R2,
in order to obtain a compound of the following formula (B):

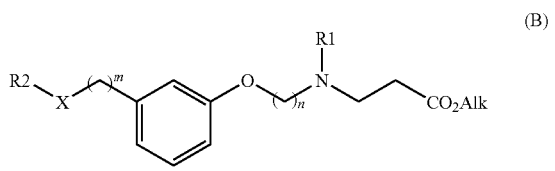

for which R1, R2, X, n, m and Alk are as defined above, (b) saponification of the terminal ester of the compound of formula (B) obtained in the previous step (a) in order to obtain a compound of the following formula (C):

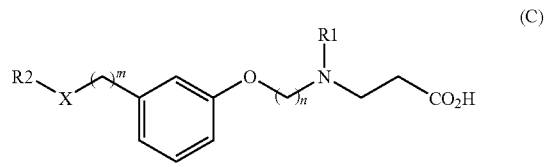

for which R1, R2, X, n and m are as defined above, (c) conversion of the free carboxylic acid function of the compound of formula (C) obtained in the previous step into a hydroxy-bisphosphonic function in order to obtain the compound of formula (I), (d) optionally salification of the compound of formula (I) obtained in the previous step (c) for obtaining a pharmaceutically acceptable salt of the latter, and (e) separation from the reaction medium of the compound of formula (I) or of one of its pharmaceutically acceptable salts obtained in the previous step (c) or (d).

Step (a):

This coupling step will be achieved between the XH (i.e. OH or OHR3) function of the compound of formula (A) and the functional group of the molecule of therapeutic or diagnostic interest as defined earlier, by techniques well-known to one skilled in the art.

This may in particular be a nucleophilic substitution, such as notably between a halogenated notably chlorinated or brominated, molecule of therapeutic or diagnostic interest, and the XH function of the compound of formula (A). Such a reaction may advantageously be achieved in the presence of a base such as $NaHCO_3$ or further NaHMDS (sodium hexamethyldisilazane).

This may also be a peptide coupling between a carboxylic acid function born by the molecule of therapeutic or diagnostic interest and the function XH born by the compound of formula (A). Such a reaction may advantageously be carried out in the presence of a coupling agent optionally associated with a coupling auxiliary agent.

The coupling agent may in particular be diisopropylcarbodiimide (DIC), dicyclohexylcarbodiimide (DCC), 1-(3-dimethylaminopropyl)-3-ethylcarbodiimide hydrochloride (EDC), carbonyldiimidazole (CDI), 2-(H-benzotriazol-1-yl)-1,1,3,3-tetramethyluronium hexafluoro-phosphate (HBTU), 2-(1H-benzotriazole-1-yl)-1,1,3,3-tetramethyluronium tetrafluoroborate (TBTU) or O-(7-azobenzotriazol-1-yl)-1,1,3,3-tetramethyluranium hexafluoro-phosphate (HATU).

The coupling auxiliary may notably be selected from N-hydroxy-succinimide (NHS), N-hydroxy-benzotriazole (HOBt), 3,4-dihydro-3-hydroxy-4-oxo-1,2,3-benzotriazole (HOOBt), 1-hydroxy-7-azabenzo-triazole (HOAt), dimethylaminopyridine (DMAP) or N-hydroxysulfo-succinimide (sulfo NHS).

Step (b):

This step may be carried out in the presence of an acid such as trifluoroacetic, formic, acetic, hydrochloric, sulfuric acid, etc., and in particular with trifluoroacetic acid.

Step (c):

This step may be carried out by techniques well-known to one skilled in the art.

It may notably be carried out by activation of the carboxylic acid function of the compound (C) in the form of its boronate derivative by action of a borane such as catecholborane, and then by reaction under Arbuzov conditions with tris(trimethylsilyl) phosphite, followed by a treatment with an aliphatic alcohol such as methanol.

By <<aliphatic alcohol>> is meant a compound including an alcohol function OH on a linear or branched and saturated or unsaturated hydrocarbon chain and advantageously including from 1 to 6, preferably from 1 to 4 carbon atoms.

Step (d):

The salification step will be carried out in the presence of a pharmaceutically acceptable acid or base as defined above.

Step (e):

The thereby obtained compound of formula (I) may be separated from the reaction medium by methods well-known to one skilled in the art, such as for example by extraction, evaporation of the solvent, or further by precipitation and filtration.

Moreover, this compound may be purified if necessary by techniques well-known to one skilled in the art, such as by re-crystallization if the compound is crystalline, by column chromatography on silica gel or further by high performance liquid chromatography (HPLC).

The compound of formula (A), used as a starting reagent, may be prepared by techniques well-known to one skilled in the art.

It may in particular be prepared according to the following successive steps:

(a1) reaction between a compound of the following formula (D):

(D)

for which m is as defined above, and a molecule of the following formula (E):

(E)

for which n is as defined above and Hal represents a halogen atom, and in particular a bromine atom, in order to obtain a compound of the following formula (F):

(F)

for which n, m and Hal are as defined above, (b1) reaction between the compound of formula (F) obtained in the previous step (a1) and a compound of the following formula (G):

(G)

for which R1 and Alk are as defined above, in order to obtain a compound of the following formula (A1):

(A1)

for which n, m, R1 and Alk are as defined above, and (c1) optionally amination of the free OH function of the compound of formula (A1) obtained in the previous step (b1) in order to obtain a compound of the following formula (A2):

(A2)

for which n, m, R1, R3 and Alk are as defined above.

Step (a1):

This coupling reaction is advantageously carried out in the presence of a base such as $K_2CO_3$.

The starting products ((D) and (E)) are either commercial products or prepared by techniques well-known to one skilled in the art.

Step (b1):

Also, this step is advantageously carried out in the presence of a base such as $K_2CO_3$.

The reagent (G) is easily synthesized by methods well-known to one skilled in the art as illustrated in the examples below.

Step (c1):

With this optional step, it is possible to have access to compounds of formula (A) for which X=NR3.

This step is carried out according to procedures well-known to one skilled in the art.

Thus, the free OH group may be converted into a leaving group such as a mesylate (notably by action of mesyl chloride in the presence of a base such as triethylamine), and then this leaving group is displaced by the amine $R3NH_2$.

DESCRIPTION OF THE APPENDED FIGURES

Figure 4:
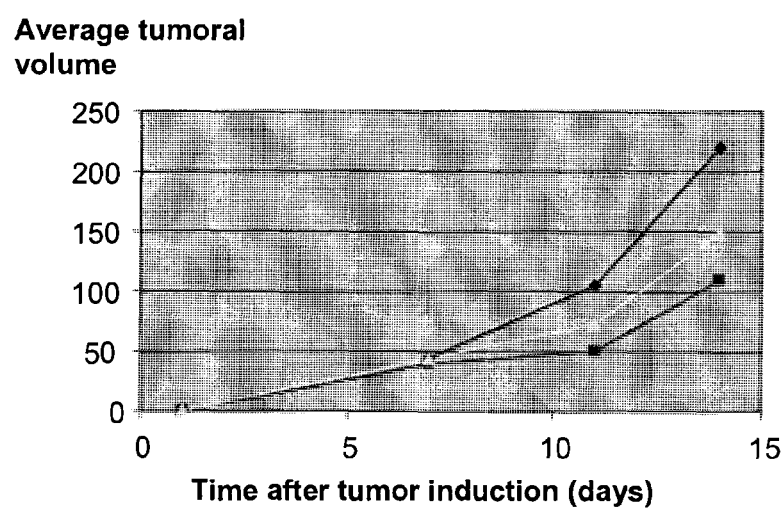

FIG. 4 illustrates the change in the size of the tumor versus time with or without a treatment at D7 with the molecule (IV) or ifosfamide (a reference chemotherapy molecule). The lozenges represent the control (i.e. absence of treatment), the squares represent the results obtained with ifosfamide used at 230 μmol/kg and the triangles represent the results obtained with the compound (IV) used at 115 μmol/kg.

Figure 5:
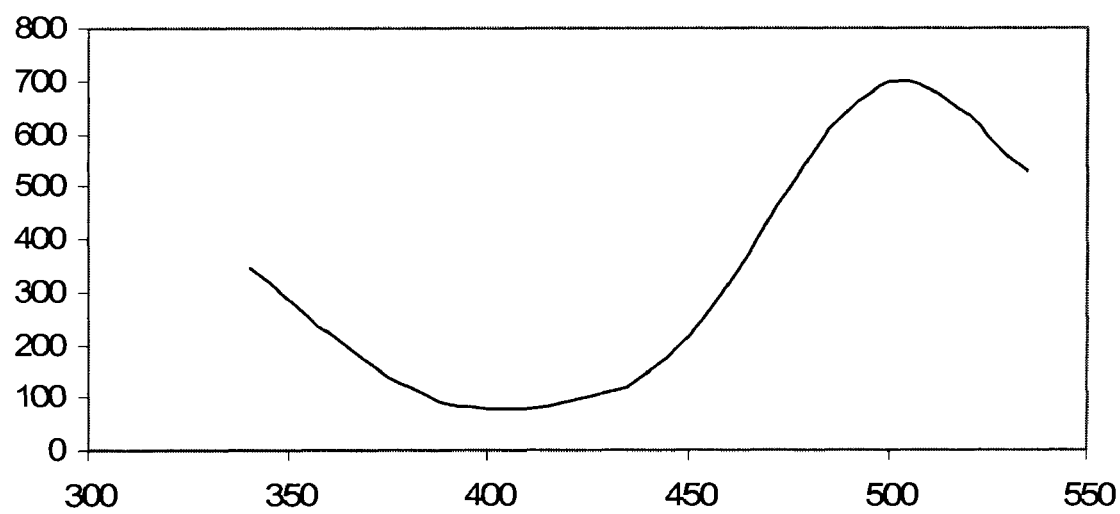

FIG. 5 illustrates the emission spectrum of the molecule (II).

ACRONYMS USED

DCM Dichloromethane
DMF Dimethylformamide
eq. Equivalent
HMDS Hexamethylsilazane
HRMS High Resolution Mass Spectrum
ppm parts per million
PTSA Para-toluenesulfonic acid
NMR Nuclear Magnetic Resonance
RT Room Temperature
TEA Triethylamine
THF Tetrahydrofurane

EXAMPLES

1. Synthesis of the Molecules 1.1. Synthesis of the Molecule of Formula (II)

The synthesis of the molecule of formula (II) was carried out in 8 steps from 3-hydroxy-benzaldehyde and from tert-butyl N-methyl-3-amino-propanoate according to the following reaction scheme:

-continued

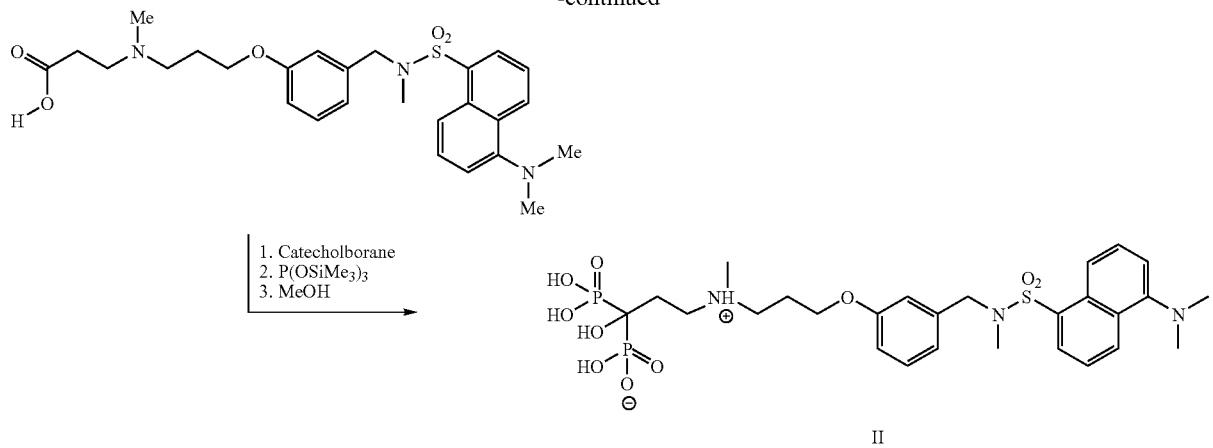

3-(hydroxy)benzyl alcohol

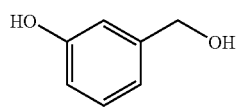

NaBH$_4$ (775 mg, 20.5 mmol) is gradually added to a solution of 3-hydroxybenzaldehyde (5 g, 40.9 mmol) in EtOH (25 mL) while cooling the reaction mixture with cold water. This mixture is stirred for 5-10 min at the same temperature. And then dichloromethane (DCM) (100 mL) is added followed by a 2M HCl aqueous solution (until pH ~3). The organic phase is separated and the final product is extracted 4 times from the aqueous phase with a EtOH/DCM mixture in the proportion of 1:3. The collected organic phases are dried on Na$_2$SO$_4$. After evaporation of the solvents under reduced pressure, a viscous colorless oil is obtained (4.9 g, 97%), which gradually crystallizes.

$^1$H NMR (CD$_3$OD, 300 MHz) δ, ppm: 7.13 (1H, t, $^3$J=9 Hz); 6.90-6.72 (2H, m); 6.71-6.60 (1H, m); 4.83 (2H, s); 4.53 (2H, s).

$^{13}$C NMR (CD$_3$OD, 300 MHz) δ, ppm: 158.65; 144.37; 130.49; 119.22; 115.26; 114.90; 65.29.

(3-(3-bromopropoxy)phenyl)methanol

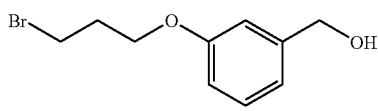 [SMILES: OCc1cccc(OCCCBr)c1]

1,3-dibromopropane (23 mL, 0.22 mol) is gradually added to a suspension of K$_2$CO$_3$ (3.2 g, 23 mmol) and 3-(hydroxymethyl)phenol (5 g, 40.3 mmol) in dimethylformamide (DMF) (30 mL) stirred beforehand for 5 min at 65° C. The reaction medium is maintained under stirring for 45 min at the same temperature. After cooling to room temperature (RT), Et$_2$O (150 mL) is added and the organic phase is extracted 4 times with a saturated NaCl aqueous solution. The organic phase is dried on Na$_2$SO$_4$. After evaporation of the solvent under reduced pressure, a viscous colorless oil is obtained (6.7 g, 68%) which gradually crystallizes.

$^1$H NMR (CDCl$_3$, 300 MHz) δ, ppm: 7.22 (1H, t, $^3$J=9 Hz); 6.94-6.83 (2H, m); 6.82-6.73 (1H, dd, $^3$J=9 Hz, J=3 Hz); 4.58 (2H, s); 4.05 (2H, t, $^3$J=6 Hz); 3.56 (2H, t, $^3$J=6 Hz); 2.46 (1H, br,s); 2.27 (2H, q, $^3$J=6 Hz).

$^{13}$C NMR (CDCl$_3$, 300 MHz) δ, ppm: 159,00; 142,74; 129.68; 119.44; 113.82; 113.01; 65.41; 65.05; 32.46; 30.17.

Tert-butyl 3-(methylamino)propanoate

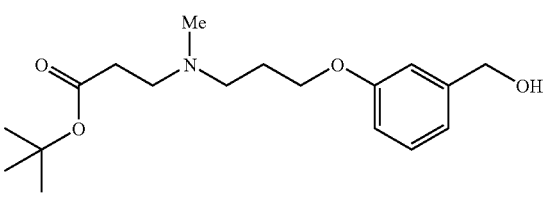 [SMILES: CN(CCCOc1cccc(CO)c1)CCC(=O)OC(C)(C)C]

Tert-butyl acrylate (3.08 g, 3.52 mL, 24 mmol) is gradually added at −45° C. to the homogeneous solution obtained from DMF (40 mL), methylammonium chloride (4.9 g, 72 mmol) and 1,8-diazabicyclo[5.4.0]undec-7-ene (DBU) (21 mL, 144 mmol). The reaction medium is maintained under stirring at −10° C. for 2hrs 30. And then Et$_2$O (200 mL) is added and the reaction mixture is extracted 4 times with a saturated NaCl aqueous solution. The organic phase is dried on Na$_2$SO$_4$. After evaporation of the solvent under reduced pressure at 30° C., a colorless oil is obtained (3.6 g, 94%).

$^1$H NMR (CDCl$_3$, 300 MHz) δ, ppm: 2.75 (2H, t, $^3$J=6 Hz); 2.42-2.32 (5H, m); 1.40 (9H, s).

$^{13}$C NMR (CDCl$_3$, 300 MHz) δ, ppm: 171.97; 80.18; 47.24; 36.16; 35.57; 27.99.

Tert-butyl 3-((3-(3-hydroxymethyl)phenoxy)propyl)(methyl)amino)propanoate

K₂CO₃ (1 g, 7.3 mmol) is added at RT to a solution of (3-(3-bromopropoxy)phenyl)methanol (1.8 g, 7.3 mmol) and of tert-butyl 3-(methylamino)propanoate (1.75 g, 11 mmol) in DMF (50 mL) containing a catalytic amount of NaI. This mixture is stirred for 48 hrs at the same temperature under argon. And then Et₂O (200 mL) is added and this solution is extracted 4 times with a saturated NaCl aqueous solution. The organic phase is dried on Na₂SO₄. After chromatography on silica (eluent—DCM:MeOH=100:1) and evaporation of the solvent under reduced pressure at 30° C., a colorless oil is obtained (1.46 g, 62%).

¹H NMR (CDCl₃, 300 MHz) δ, ppm: 7.18 (1H, t, ³J=9 Hz); 6.93-6.80 (2H, m); 6.79-6.68 (1H, dd, ³J=9 Hz, J=3 Hz); 4.57 (2H, s); 3.92 (2H, t, ³J=6 Hz); 3.22 (1H, br s); 2.62 (2H, t, ³J=6 Hz); 2.45 (2H, t, ³J=6 Hz); 2.32 (2H, t, ³J=6 Hz); 2.17 (3H, s); 1.86 (2H, q, ³J=6 Hz); 1.39 (9H, s).

¹³C NMR (CDCl₃, 300 MHz) δ, ppm: 172.12; 159.30; 143.04; 129.52; 119.07; 113.74; 112.91; 80.51; 66.15; 64.95; 54.07; 52.96; 41.98; 33.62; 28.20; 27.17.

Tert-butyl 3-(methyl(3-(3-((methylamino)methyl)phenoxy)-propyl)-amino)proanoate

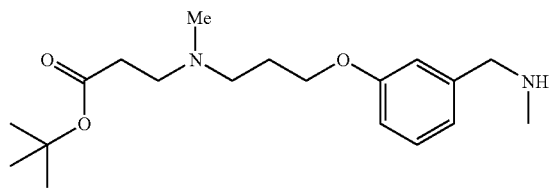 [SMILES: CNCc1cccc(OCCCN(C)CCC(=O)OC(C)(C)C)c1]

Methane-sulfonyl chloride (MsCl) (0.555 mL, 7.2 mmol) is gradually added at −78° C. to a solution of tert-butyl 3-((3-(3-(hydroxymethyl)-phenoxy)propyl)(methyl)amino)propanoate (465 mg, 1.44 mmol) and of triethylamine (TEA) (1.4 mL, 10 mmol) in dichloromethane (20 mL). This mixture is stirred for 1 hr 30 min at the same temperature under argon. And then methylamine (0.65M solution in dichloromethane, 22 mL, 14.3 mmol) is added; the mixture is left to return to room temperature and is stirred at this temperature for further 1 hr. The obtained mixture is extracted 4 times with a mixed aqueous solution of NaCl with NaHCO₃. The organic phase is dried on Na₂SO₄. After evaporation of the solvent under reduced pressure, the final crude product is obtained as a colorless oil (455 mg, 94%), which is used without any additional purification for the next step.

¹H NMR (CDCl₃, 300 MHz) δ, ppm: 7.30 (1H, t, J=8 Hz); 7.11 (1H, s); 7.02 (1H, d, J=6 Hz); 6.96 (1H, d, J=6 Hz); 4.55 (2H, s); 4.07 (2H, t, J=6 Hz); 3.0-2.83 (4H, m); 2.69 (3H, s); 2.60 (2H, t, J=6 Hz); 2.52 (3H, s); 2.10 (2H, q, J=6 Hz); 1.40 (9H, s).

¹³C NMR DEPT-135 (CDCl₃, 300 MHz) δ, ppm: 130.49; 124.30; 118.92; 116.54; 66.11; 61.06; 53.83; 52.65; 41.52; 39.54; 32.87; 28.06; 26.32.

Tert-butyl 3-((3-(3-(((5-(dimethylamino)naphthalen-1-yl)(methyl)amino)methyl)phenoxy)propyl)(methyl)amino)-propanoate

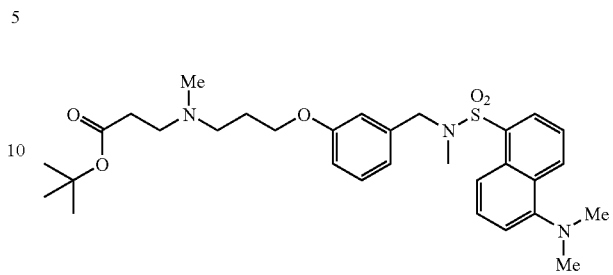

The NaHCO₃ solution (133 mg, 1.58 mmol) in water (2 mL) is added at RT to the solution of crude tert-butyl 3-(methyl(3-(3-((methylamino)methyl)phenoxy)propyl)amino)propanoate (455 mg, 1.35 mmol) and of dansyl chloride (364 mg, 1.35 mmol) in acetonitrile (35 mL). This mixture is stirred for 1 h 30 at the same temperature under argon. And the solvent is then evaporated under reduced pressure and the obtained oil is purified by chromatography on silica gel (eluent—DCM followed by the mixture DCM:MeOH=100:1). The final product is obtained as a fluorescent pale green amorphous gum (522 mg, 68%).

¹H NMR (CDCl₃, 300 Mz) δ, ppm: 8.58 (1H, d, J=9 Hz); 0.46 (1H, d, J=9 Hz); 8.26 (1H, d, J=6 Hz); 7.65-0.50 (2H, m); 7.28-7.15 (2H, m); 6.87-6.70 (3H, m); 0.32 (2H, s); 3.87 (2H, t, J=6 Hz); 2.92 (6H, s); 2.80-2.63 (5H, m); 2.55 (2H, t, J=6 Hz); 2.43 (2H, t, J=6 Hz); 2.29 (3H, s); 1.93 (2H, q, J=6 Hz); 1.46 (9H, s).

¹³C NMR (CDCl₃, 300 MHz) δ, ppm: 172.08; 159.47; 151.97; 137.52; 134.07; 130.72; 130.46; 130.42; 130.27; 129.70; 128.27; 123.37; 120.70; 119.91; 115.36; 114.38; 114.13; 80.55; 66.07; 54.18; 53.65; 53.13; 45.61; 42.08; 33.91; 33.77; 28.28; 27.24.

3-((3-(3-((5-(dimethylamino)-N-methylnaphthalene-1-sulfonamido)methyl)phenoxy)propyl)(methyl)amino)propanoic acid

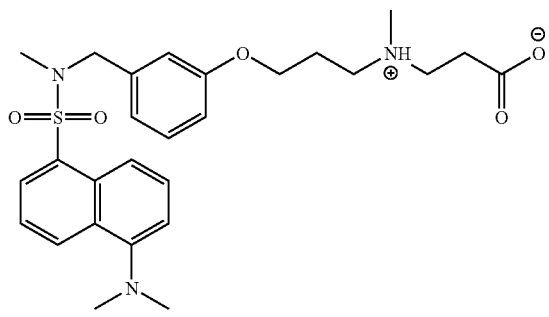 [SMILES: CN(C)c1cccc2c(S(=O)(=O)N(C)Cc3cccc(OCCC[NH+](C)CCC(=O)[O-])c3)cccc12]

Trifluoroacetic acid (2 mL) is added to a solution of tert-butyl 3-((3-(3-(((5-(dimethylamino)naphthalen-1-yl)(methyl)amino)methyl)phenoxy)propyl)(methyl)amino)-propanoate (100 mg, 0.175 mmol) in dichloromethane (4 mL) at RT. This mixture is stirred for 4.5 hrs at the same temperature. And then the solvent is co-evaporated with dichloromethane under reduced pressure and the obtained oil is purified by chromatography on a column of silica gel (eluent—DCM followed by the mixture DCM:MeOH=10:1). The final product is obtained as a fluorescent pale green amorphous gum (90 mg, 99%).

$^1$H NMR (CDCl$_3$-MeOD, 300 MHz) δ, ppm: 8.60-8.45 (2H, m); 8.17 (1H, d, J=6 Hz); 7.65-7.50 (2H, m); 7.37 (1H, d, J=6 Hz); 7.12 (1H, t, J=6 Hz); 6.80-6.65 (3H, m); 4.25 (2H, s); 3.87 (2H, t, J=6 Hz); 3.35-3.10 (4H, m); 3.00 (6H, s); 2.85-2.70 (5H, m); 2.65 (3H, s); 2.14 (2H, m).

$^{13}$C NMR (CDCl$_3$-MeOD, 300 MHz) δ, ppm: 172.23; 158.51; 148.22; 137.45; 134.27; 130.28; 130.11; 129.77; 129.47; 129.02; 128.02; 124.32; 121.80; 121.18; 116.38; 114.03; 113.93; 64.46; 54.39; 53.42; 51.81; 45.76; 40.18; 33.95; 28.84; 23.89.

3-((3-(3-((5-dimethylamino)-N-methylnaphthalene-1-sulfonamido)methyl)phenoxy)propyl(methyl)amino)-1-hydropropane-1,1-diyldiphosphonic acid
(II)

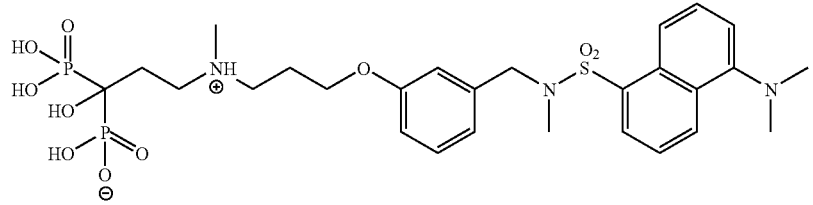 [SMILES: CN(C)c1cccc2c(S(=O)(=O)N(C)Cc3cccc(OCCC[NH+](C)CCC(O)(P(=O)([O-])O)P(=O)(O)O)c3)cccc12]

A solution of catecholborane (1M in THF, 1.07 mL, 1.07 mmol, 6.1 eq.) was added on 3-((3-(3-((5-(dimethylamino)-N-methylnaphthalene-1-sulfonamido)methyl)phenoxy)propyl)(methyl)amino)propanoic acid (90 mg, 0.175 mmol, 1 eq.) under argon at RT under dry conditions. This mixture is stirred for 1 hr at the same temperature until the end of gas evolvement (H$_2$). And then P(OSiMe$_3$)$_3$ (371 mg, 1.24 mmol, 7.1 eq.) was added pure, and stirring was maintained for 16 hrs. Methanol (0.5 mL) is added, the reaction medium is stirred for 1hr and then diluted with DCM (15 mL). A white precipitate forms. It is filtered, rapidly rinsed with DCM and dried under argon. 60 mg of a hygroscopic fluorescent white powder is obtained, which will be purified on a silica gel column (silica gel 100 C18-Reversed phase, eluent H$_2$O: MeOH).

$^1$H NMR (D$_2$O-Py-DMSO-MeOD, 300 MHz) δ, ppm: 8.33 (1H, d, J=6 Hz); 8.17 (1H, d. J=6 Hz); 8.02 (1H, d, J=6 Hz); 7.60-7.40 (2H, m); 7.11 (1H, d, J=6 Hz); 7.05 (1H, t, J=6 Hz); 6.73 (1H, d, J=6 Hz); 6.64 (1H, d, J=6 Hz); 6.59 (1H, s); 4.13 (2H, s); 3.79 (2H, t, J=6 Hz); 3.37 (2H, m); 2.78 (3H, s); 2.64 (6H, s); 2.56 (3H, s); 2.55-2.20 (4H, m); 2.08 (2H, m).

$^{13}$C NMR (D$_2$O, 300 MHz) δ, ppm: 158.25; 151.26; 137.14; 133.93; 130.06 (sl); 129.74 (sl); 129.38; 128.20 (sl); 126.51 (sl); 123.53 (sl); 120.50 (sl); 119.17 (sl); 115.17 (sl); 114.24 (sl); 113.84 (sl); 72.12 (t, J=132 Hz); 64.81; 53.50; 53.04; 44.71; 39.29; 38.74; 33.60; 28.07; 23.64.

$^{31}$P NMR (D$_2$O-Py-DMSO-MeOD, 300 MHz) δ, ppm: 16

HRMS (ES) (m/z): [M+H] calculated for C$_{27}$H$_{39}$N$_3$O$_{10}$P$_2$S 660.1910, found 660.1911

1.2. Synthesis of the Molecule of Formula (III)

The synthesis is carried out from the molecule 3, the synthesis procedure of which is described below (see 1.4.).

3-((3-(3-((amino(bis(2-chloroethyl)amino)phosphoryloxy)methyl)phenoxy)propyl)(methyl)amino)propanoic acid

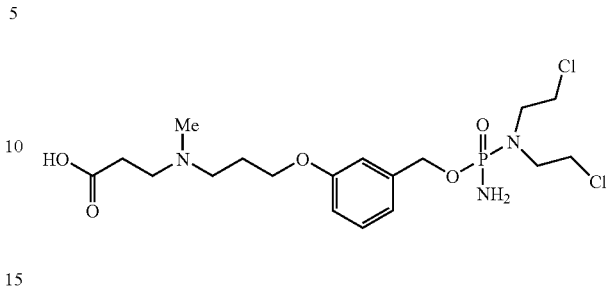

Trifluoroacetic acid (TFA) (20 mL) is added to a solution of the molecule 3 (1.08 g, 2.05 mmol) in MeNO$_2$ (160 mL) and the obtained solution is stirred for 30 min at RT. The solvent is evaporated for 10 min at RT and dry-evaporated at 40° C., and then taken up in DCM in order to remove the traces of TFA. The residue is rapidly chromatographed on a silica gel column (40 cm$^3$, DCM gradient up to DCM/MeOH (1:1)) in order to obtain a colorless oil (267 mg, 33%).

$^1$H NMR (CD$_3$OD, 300 MHz) δ, ppm: 7.29 (1H, t, J=7 Hz), 7.08-6.87 (3H, m), 4.96 (2H, d, J=8 Hz), 4.14 (2H, t, J=7 Hz), 3.70-3.55 (4H, m), 3.50-3.30 (8H, m), 2.89 (3H, s), 2.59 (2H, t, J=7 Hz), 2.26 (2H, m).

$^{13}$C NMR (CD$_3$OD, 300 MHz) δ, ppm: 177.63; 160.24; 140.12 (d, J=7 Hz); 130.88; 121.45; 115.61; 114.86; 68.09 (d, J=5 Hz); 66.36; 55.20; 55.04; 50.81 (d, J=5 Hz); 43.24; 40.35; 31.22; 25.57.

$^{31}$P NMR (D$_2$O, 300 MHz) δ, ppm: 20

HRMS (ES) (m/z): [M+H]$^+$calculated for C$_{18}$H$_{30}$Cl$_2$N$_3$O$_5$P 470.1378, found: 470.1377

3-((3-(3-((amino(bis(2-chloroethyl)amino)phosphoryloxy)methyl)phenoxy)propyl)(methyl)amino)-1-hydroxypropane-1,1-diyl-diphosphonic acid (III)

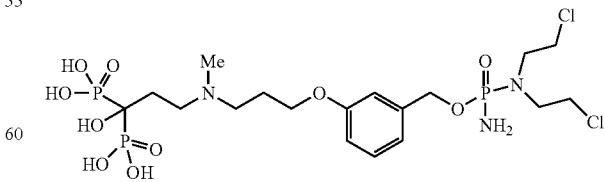

The same procedure as the one used for the synthesis of molecule (II) (last step) is applied, however by using a solution of 230 mg of 3-((3-(3-((amino(bis(2-chloroethyl)amino) phosphoryloxy)-methyl)phenoxy)propyl)(methyl)amino)

propanoic acid in 6.5 mL of THF, 5.1 eq. mol. of catecholborane and 6.1 eq. mol. of P (OSiMe$_3$)$_3$. A colorless product is isolated with a yield of 32%.

$^1$H NMR (D$_2$O, 300 MHz) δ, ppm: 7.36 (1H, t, J=7 Hz), 7.11-6.92 (3H, m), 4.97 (2H, d, J=8 Hz), 4.15 (2H, t, J=7 Hz), 3.72-3.56 (4H, m), 3.56-3.10 (8H, m), 2.86 (3H, s), 2.33 (2H, m), 2.21 (2H, m).

NMR (D$_2$O, 300 MHz) δ, ppm: 158.16; 138.10 (d, J=7 Hz); 130.19; 120.82; 115.00; 113.98; 72.10 (t, $^1J_{C-P}$=130 Hz); 67.31 (d, J=5 Hz); 65.35; 53.62; 53.29 (t, J=7 Hz); 47.93 (d, J=5 Hz); 42.06; 39.55; 27.95; 23.67.

$^{31}$P NMR (D$_2$O, 300 MHz) δ, ppm: 20 (1P), 18 (2P)

HRMS (ES) (m/z): [M+H]$^+$ calculated for C$_{18}$H$_{34}$Cl$_2$N$_3$O$_{10}$P$_3$ 638.0734, found: 638.0733.

1.3. Synthesis of the Molecule of Formula (IV)

2-(3-(3-bromopropoxy)benzyloxy)ethanol

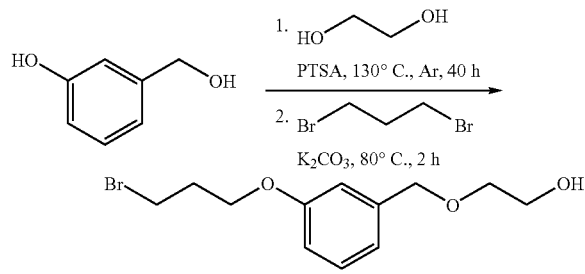

The solution of 3-(hydroxymethyl)phenol (8.8 g, 71 mmol) and of paratoluenesulfonic acid (PTSA) (2.3 g, 13.4 mmol) in ethylene glycol (180 mL) is heated to 130° C. under argon for 40 hrs. After cooling down to 80° C., K$_2$CO$_3$ (13 g, 94 mmol) and then 1,3-dibromopropane (42 mL, 386 mmol) are added. After 2 hrs of stirring at this temperature, the reaction is cooled to RT and extracted with a DCM-H$_2$O mixture. And then the organic phase is washed several times with water, dried on Na$_2$SO$_4$ and concentrated in vacuo. The final crude product is obtained as a yellow oil (14 g, 68% for two steps) and used without any further purification.

$^1$H NMR (CDCl$_3$, 300 MHz) δ, ppm: 7.28 (1H, t, J=7 Hz), 7.00-6.90 (2H, m), 6.85 (1H, dd, J=3 Hz, J=7 Hz), 4.54 (2H, s), 4.11(2H, t, J=7 Hz), 3.77 (2H, t, J=6 Hz), 3.68-3.52 (4H, m), 2.62 (1H, br s), 2.32 (2H, q, J=7 Hz).

$^{13}$C NMR (CDCl$_3$, 300 MHz) δ, ppm: 158.97; 139.73; 129.66; 120.36; 113.95; 113.92; 73.20; 71.56; 65.35; 61.91; 32.46; 30.21.

Tert-butyl 3-((3-(3-((2-hydroxyethoxy)methyl)phenoxy)propyl)(methyl)amino)propanoate

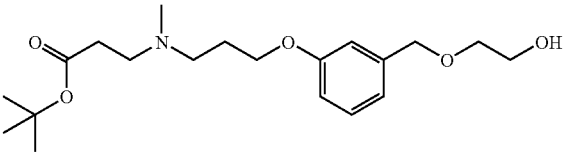 [SMILES: CN(CCCOc1cccc(COCCO)c1)CCC(=O)OC(C)(C)C]

The same procedure as the one described for the preparation of tert-butyl 3-((3-(3(hydroxymethyl)phenoxy)propyl)(methyl)amino)propanoate is applied. A colorless product is isolated with a yield of 68%.

$^1$H NMR (CDCl$_3$, 300 MHz) δ, ppm: 7.20 (1H, t, J=7 Hz), 6.90-6.81 (2H, m), 6.78 (1H, dd, J=3 Hz, J=7 Hz), 4.48 (2H, s), 3.96 (2H, t, J=7 Hz), 3.71 (2H, t, J=6 Hz), 3.54 (2H, t, J=6 Hz), 2.65 (2H, t, J=7 Hz), 2.59 (1H, br s), 2.49 (2H, t, J=7 Hz), 2.35 (2H, t, J=7 Hz), 2.21 (3H, s), 1.90 (2H, q, J=7 Hz), 1.40 (9H, s).

$^{13}$C NMR (CDCl$_3$, 300 MHz) δ, ppm: 172.13; 159.32; 139.69; 129.54; 119.97; 113.97; 113.87; 80.46; 73.26; 71.56; 66.17; 61.93; 54.11; 53.10; 42.08; 33.78; 28.23; 27.28.

Tert-butyl N-(3-(3-[6-amino-9-chloro-7-(2-chloroethyl)-6-oxido-2,5-dioxa-7-aza-6-phosphanon-1-yl]phenoxy)propyl)-N-methyl-β-alaninate

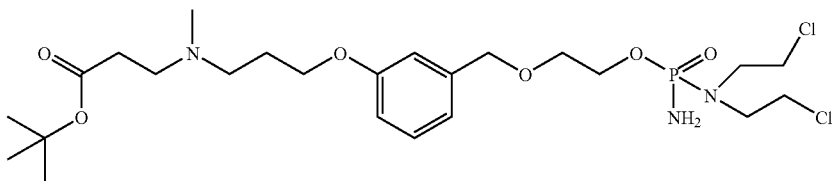 [SMILES: CN(CCCOc1cccc(COCCOP(N)(=O)N(CCCl)CCCl)c1)CCC(=O)OC(C)(C)C]

The same procedure than the one described for the preparation of the molecule 3 is applied. A colorless product is isolated with a yield of 65%.

$^1$H NMR (CDCl$_3$, 300 MHz) δ, ppm: 7.20 (1H, t, J=7 Hz), 6.91-6.81 (2H, m), 6.78 (1H, dd, J=3 Hz, J=7 Hz), 4.48 (2H, s), 4.19 (1H, m), 4.02 (1H, m), 3.95 (2H, t, J=7 Hz), 3.70-3.50 (6H, m), 3.97-3.28 (4H, m), 3.06 (2H, br d, J=3 Hz), 2.65 (2H, t, J=7 Hz), 2.50 (2H, t, J=7 Hz), 2.35 (2H, t, J=7 Hz), 2.21 (3H, s), 1.90 (2H, q, J=7 Hz), 1.39 (9H, s).

$^{13}$C NMR (CDCl$_3$, 300 MHz) δ, ppm: 172.07; 159.34; 139.23; 129.65; 120.05; 114.05; 114.02; 80.48; 73.28; 69.53 (d, J=6 Hz); 66.18; 64.75 (d, J=4 Hz); 54.11; 53.11; 49.62; 49.57; 42.68; 42.05; 33.77; 28.23; 27.28.

N-(3-{3-[6-amino-9-chloro-7-(2-chloroethyl)-6-oxido-2,5-dioxa-7-aza-6-phosphanon-1-yl]phenoxy}propyl)-N-methyl-β-alanine $^{31}$P NMR (D$_2$O, 300 MHz) δ, ppm: 20 (1P), 18 (2P).

HRMS (ES) (m/z): [M+H]$^-$ calculated for C$_{20}$H$_{38}$Cl$_2$N$_3$O$_{11}$P$_3$ 658.1018, found: 658.1018.

$^{13}$C NMR (D$_2$O, 300 MHz) δ, ppm: 158.13; 139.11; 130.07; 121.47; 114.63; 72.58; 72.11 (t, $^1J_{C-P}$=130 Hz); 69.00 (d, J=7 Hz); 65.34; 64.84 (d, J=4 Hz); 53.65; 53.32 (t, J=6 Hz); 47.97; 47.92; 42.08; 39.56; 27.96; 23.71.

1.4. Synthesis of Simplified Molecules of the Invention

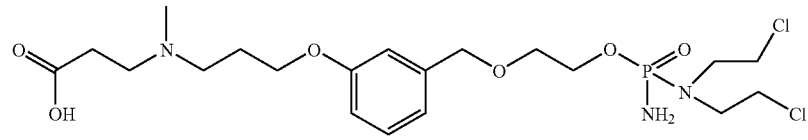 [SMILES: CN(CCCOc1cccc(COCCOP(N)(=O)N(CCCl)CCCl)c1)CCC(=O)O]

The same procedure as the one described for the preparation of 3-((3-(3-((amino(bis(2-chloroethyl)amino)phosphoryloxy)methyl)phenoxy)propyl)(methyl)amino)propanoic acid is applied. A colorless product is isolated with a yield of 73%.

$^1$H NMR (CD$_3$OD, 300 MHz) δ, ppm: 7.26 (1H, t, J=1 Hz), 7.02-6.92 (2H, m), 6.89 (1H, dd, J=3 Hz, J=7 Hz), 4.54 (2H, s), 4.60-4.02 (4H, m), 3.77-3.56 (6H, m), 3.50-3.30 (8H, m), 2.89 (3H, s), 2.59 (2H, t, J=7 Hz), 2.25 (2H, m).

$^{13}$C NMR (CD$_3$OD, 300 MHz) δ, ppm: 177.58; 160.22; 141.26; 130.73; 121.80; 115.18; 115.10; 74.12; 70.73 (d, J=7 Hz); 66.27; 66.03 (d, J=4 Hz); 55.18; 54.99; 50.88; 43.28; 40.40; 31.26; 25.59.

{3-[(3-{3-[6-amino-9-chloro-7-(2-chloroethyl)-6-oxido-2,5-dioxa-7-aza-6-phosphanon-1-yl]phenoxy}propyl)(methyl)amino]-1-hydroxypropane-1,1-diyl}biphosphonic acid (IV)

Molecular 1:

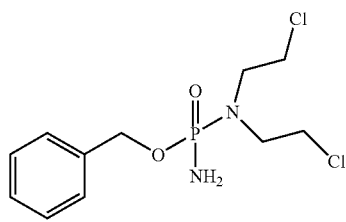

In a flask cooled by an ice bath (0° C.), equipped with a condenser and magnetic stirring, under an inert atmosphere, 484 mg of hexamethyldisilazane (3 mmol, 1 eq.) are put into solution in 10 mL of anhydrous THF. 10 min after addition at 0° C. of 2.0 mL of nBuLi (1.6 M in hexane), 1.2 eq. of this solution is transferred by cannulation into a flask containing

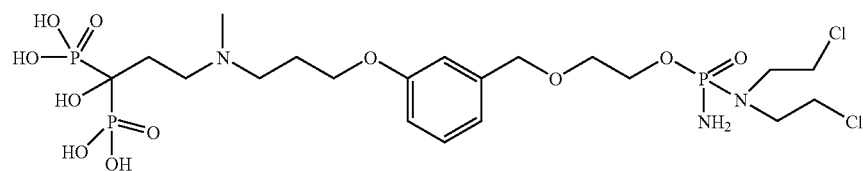 [SMILES: CN(CCCOc1cccc(COCCOP(N)(=O)N(CCCl)CCCl)c1)CCC(O)(P(=O)(O)O)P(=O)(O)O]

The same procedure as the one used for the preparation of {3-((3-(3((amino(bis(2-chloroethyl)amino)phosphoryloxy)methyl)phenoxy)propyl)(methyl)amino)-1-hydroxypropane-1,1-diyl}bisphosphonic acid is applied. A colorless product is isolated with a yield of 47%.

$^1$H NMR (D$_2$O, 300 MHz) δ, ppm: 7.38 (1H, t, J=7 Hz), 7.13-6.91 (3H, m), 4.59 (2H, s), 4.30-4.00 (4H, m), 3.78 (2H, m), 3.72-3.60 (4H, m), 3.60-3.20 (8H, m), 2.88 (3H, s), 2.35 (2H, m), 2.24 (2H, m).

324 mg of benzyl alcohol (3 mmol, 1 eq.) in solution in 10 mL of anhydrous THF. After 10 min at 0° C., the thereby formed alcoholate is transferred by cannulation into a flask containing 777 mg of dichloro-N,N-bis-(2-chloroethyl)phosphoramide (3 mmol, 1 eq.) dissolved in 20 mL of anhydrous THF. Stirring is continued for 2 hrs at 0° C. After cooling to −78° C., the reaction medium is subject to ammonia gas bubbling for 30 min. Degassing of the dissolved ammonia in the solution is carried out for 30 min at RT before evaporation under reduced pressure of the solvent. The product is directly purified by chromatography on silica gel column (eluent: CH₂Cl₂/MeOH=98:2). A transparent oil which crystallizes under cold conditions (freezer) is thereby obtained (312 mg, yield=34%). The product is re-crystallized from isopropyl ether.

¹H NMR (CDCl₃, 300 MHz) δ, ppm: 7.34 (s, 5H); 5.08-4.97 (m, 2H); 3.67-3.56 (m, 4H); 3.49-3.35 (m, 4H); 2.89 (s, 2H, NH₂).

Molecule 2:

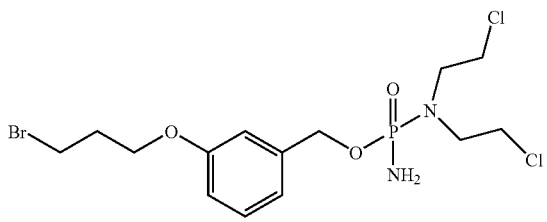

This molecule was prepared according to the synthesis procedure described for the molecule 3, from 3-(3-bromopropoxy)benzyl alcohol. After purification by chromatography on a silica gel column (eluent; DCM/MeOH 99:1); the desired product is isolated with a yield of 66%.

Rf=0.15 (eluent CH₂Cl₂/MeOH 99:1)

¹H NMR (CDCl₃, 300 MHz) δ, ppm: 7.29 (t, J=8.4 Hz, 1H); 6.96 (d, J=8.4 Hz, 1H); 6.94 (s, 1H); 6.87 (d, J=8.4 Hz, 1H); 5.07-4.93 (m, 2H); 4.12 (t, J=6 Hz, 2H); 3.65-3.59 (m, 6H); 3.48-3.39 (m, 4H); 2.71 (s, 2H); 2.32 (m, J=6 Hz, 2H).

³¹P NMR (CDCl₃, 300 MHz) δ, ppm: 15.85 (s).

Molecule 3:

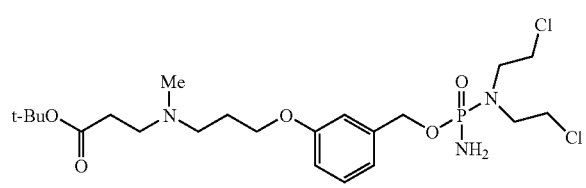

A solution of NaHMDS (2M in THF, 1.12 mL, 2.22 mmol) is added at −78° C. under argon to a solution of tert-butyl 3-((3-(3-(hydroxymethyl)phenoxy)propyl)(methyl)-amino)propanoate (600 mg, 1.86 mmol) in anhydrous THF (15 mL). After 5 min of stirring at −78° C., the reaction medium is stirred at RT for 15 min and again cooled down to −78° C. At this temperature, dichloro-N,N-bis(2-chloroethyl)phosphoramide (480 mg, 1.86 mmol) in a solution of anhydrous THF (3 mL) is added dropwise and the reaction medium is stirred for 4 hrs while allowing the temperature to rise slowly up to room temperature, which causes appearance of an insoluble material. The reaction mixture is again cooled down to −50° C. and an ammonia solution (1M in DCM, 6 mL, 6 mmol) is added. After stirring at RT for 2 hrs, DCM (120 mL) is added and the solvent is evaporated under reduced pressure. After chromatography on silica gel (eluent: DCM then DCM:MeOH=5:1) the expected product is obtained as a colorless oil (598 mg, yield=60%).

¹H NMR (CDCl₃, 300 MHz) δ, ppm: 7.23 (1H, t, J=8 Hz); 6.94-6.77 (2H, m); 5.06-4.82 (2H, m); 3.97 (2H, t, J=7 Hz); 3.65-3.50 (4H, m); 3.96-3.27 (4H, m); 2.87 (2H, br s); 2.65 (2H, t, J=7 Hz); 2.49 (2H, t, J=7 Hz); 2.35 (2H, t, J=7 Hz); 2.21 (3H, s); 1.90 (2H, q, J=7 Hz); 1.40 (9H, s).

¹³C NMR (CDCl₃, 300 MHz) δ, ppm: 172.16; 159.40; 138.09 (d, ³J_{C-P}=7 Hz); 129.84; 119.97; 114.61; 113.95; 80.51; 67.20 (d, ²J_{C-P}=5 Hz); 66.26; 54.10; 53.15; 49.40 (d, ²J_{C-P}=5 Hz); 42.73; 42.13; 33.85; 28.27; 27.31.

³¹P NMR (CDCl₃, 300 MHz) δ, ppm: 16.

Molecule 4:

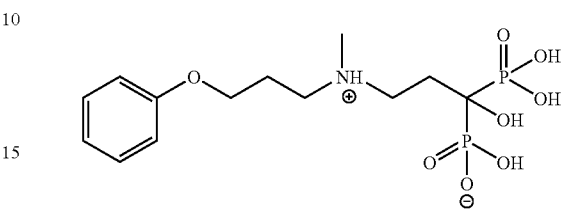

A solution of catecholborane (1M in THF, 2.1 eq.) is added onto 3-[methyl-(3-phenoxypropyl)amino]-propanoic acid (1 eq.) under argon at RT. This mixture is stirred for 1 hr at the same temperature until the end of gas evolvement (H₂). And then P(OSiMe₃)₃ (3.1 eq.) is added pure, and stirring is continued for 16 hrs. Methanol (2 mL) is added and the reaction mixture is stirred for 1 h, dry-evaporated in vacuo, dissolved in a minimum of methanol and diluted with diethyl ether (30 mL). A white precipitate forms. The latter is separated, rapidly rinsed with diethyl ether, and dried under argon. A white powder is thereby obtained with a yield of 85%.

¹H NMR (DMSO-d₆, 300 MHz) δ, ppm: 7.30-7.15 (2H, m); 7.23 (2H, t, J=7 Hz); 6.97-6.80 (3H, m); 3.99 (2H, t, J=6 Hz); 3.55-3.00 (4H, m); 2.74 (3H, s); 2.35-1.95 (4H, m).

¹³C NMR (CD₃COD₃, 300 MHz) δ, ppm: 158.87; 130.16; 121.64; 115.18; 72.33 (t, ¹J_{C-P}=136 Hz); 65.51; 54.31; 53.37; 40.37; 28.28; 24.44.

³¹P NMR (DMSO-d₆, 300 MHz) δ, ppm: 19.

2. Biological Tests 2.1. Molecules with Anti-Tumoral Activity

The three following molecules, illustrating <<simplified molecules>> of the invention, were tested for their anti-tumoral activity:

1

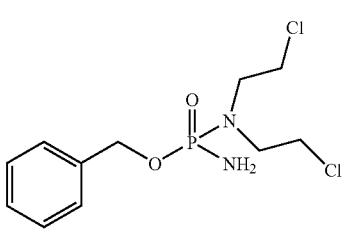

2

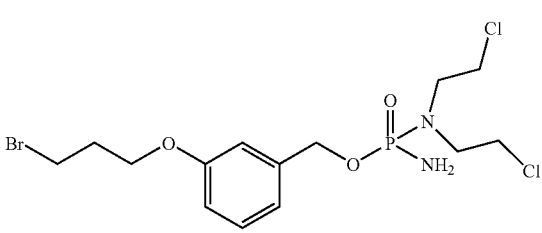

-continued

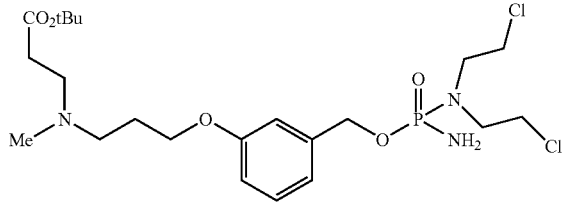

3

In Vitro Test:

A study was conducted in parallel on a line of tumoral cells (POS-1 mouse osteosarcoma) and a line of non-tumoral cells with a high proliferation rate (murine fibroblast L929). The cells were cultivated in 96-well plates for 72hrs in the presence of the molecules 1-3 to be tested and by using DMSO or ethanol as a solvent (final 1% in the well).

The following table shows the obtained results (values of the measured IC50s) for the different molecules and cell lines.

|  | L929 (DMSO) | POS-1 (DMSO) | L929 (ethanol) | POS-1 (ethanol) |
| --- | --- | --- | --- | --- |
| Molecule 1 | 500 μM | >500 μM | >500 μM | >500 μM |
| Molecule 2 | >>500 μM | 200 μM | 250 μM | 300 μM |
| Molecule 3 | 500 μM | 280 μM | >500 μM | 500 μM |

These results actually show the inhibitory activity on cell proliferation of the molecules 2 and 3 by the phosphorodiamide alkylating portion of the molecule.

In Vivo Test:

5 week old male mice of the C3H/HeN strain each receive 150,000 cells of POS-1 mouse osteosarcoma via an intravenous route in the retro-orbitary sinus, inducing development of lung nodules within 4-6 weeks.

These mice were then treated with an injection of molecules 1 or 2 (112 nmol/kg), 7 days after the injection of osteosarcoma tumoral cells.

Figure 1:
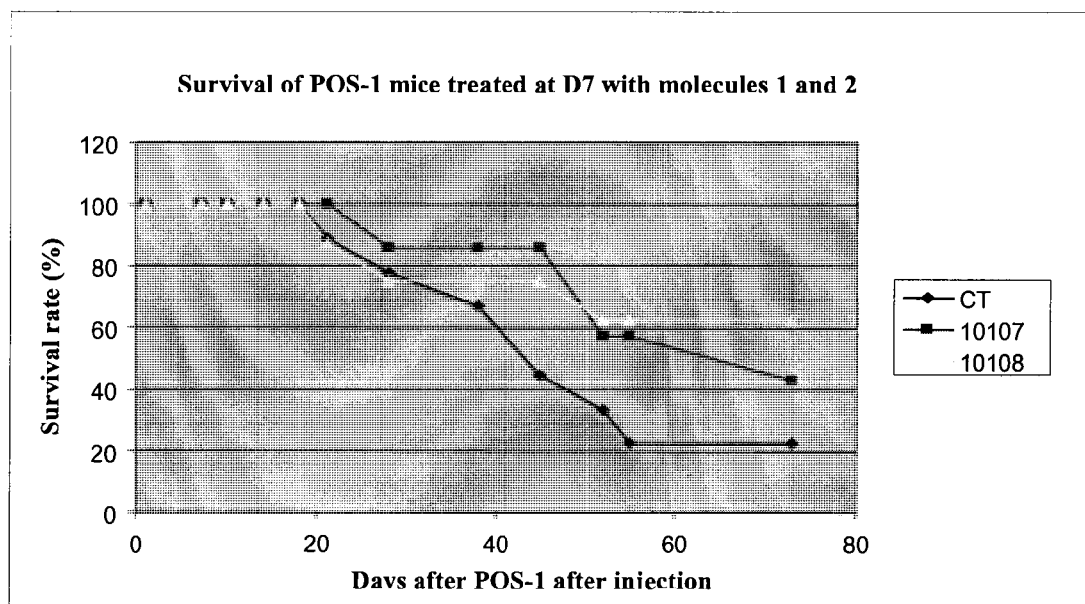
FIG. 1 illustrates the survival rate of treated mice, or not, with <<simplified molecules>> 1 and 2 of the invention, after injection of tumoral cells, versus the number of days after injection of these cells.

The results of the survival rates, shown in FIG. 1, show significant increase of this survival rate as soon as the 40$^{th}$ day after injection of the tumoral cells in the mice treated with the molecules 1 and 2 (curve with squares and with triangles in FIG. 1 respectively), comparatively with control mice which did not receive any treatment (CT curve with the lozenges in FIG. 1). The molecules 1 and 2 therefore actually have anti-tumoral activity in this model of lung nodules.

Both tests further show that the residue R2, which here is an alkylating active ingredient of the phosphorodiamide type, was released out since otherwise it will not have been able to play its role of alkylating agent and therefore of anti-tumoral agent. Therefore this shows that when m=1 and X=O, the molecule is less stable and it is then possible to release the active ingredient.

The molecules (III) and (IV) according to the invention were also tested for their anti-tumoral activity.

In Vitro Test:

The biological activities (viability/cytotoxicity test) of the molecules (III) and (IV) were tested in vitro on cultures of human, murine and rat osteosarcoma lines in comparison with normal cells (healthy osteoblasts from mouse calvaria).

The results obtained in vitro demonstrated a proliferation-inhibiting activity of the tested compounds due to death induction and therefore to cytotoxic activity of the compounds. No cytotoxic activity was observed on healthy osteoblast cells from a primary culture of mouse calvaria, thus demonstrating the non-reactivity of normal osteoblasts towards these compounds.

The following table shows the obtained results (values of the measured IC50s) for three human (MG63), mouse (POS1) and rat (OSRGA) osteosarcoma cell lines.

|  | POS1 | OSRGA | MG63 |
| --- | --- | --- | --- |
| Molecule (III) | >200 μM | >200 μM | >200 μM |
| Molecule (IV) | >500 μM | >500 μM | >500 μM |

In Vivo Tests:

Mouse osteosarcoma POS1 cells were injected in the pad of a 5-week old male mouse of the C3H/HeN strain. Fragments of the tumor which develops on this site are then transplanted into a para-osteal site in order to induce development of an osteolytic primitive bone tumor. The molecule (IV) was then injected as a cure of intraparenteral injections (IP) of 11.5 or 115 μmol/kg at 24 hr intervals from the 7$^{th}$ day (D7) after tumoral induction.

Figure 3:
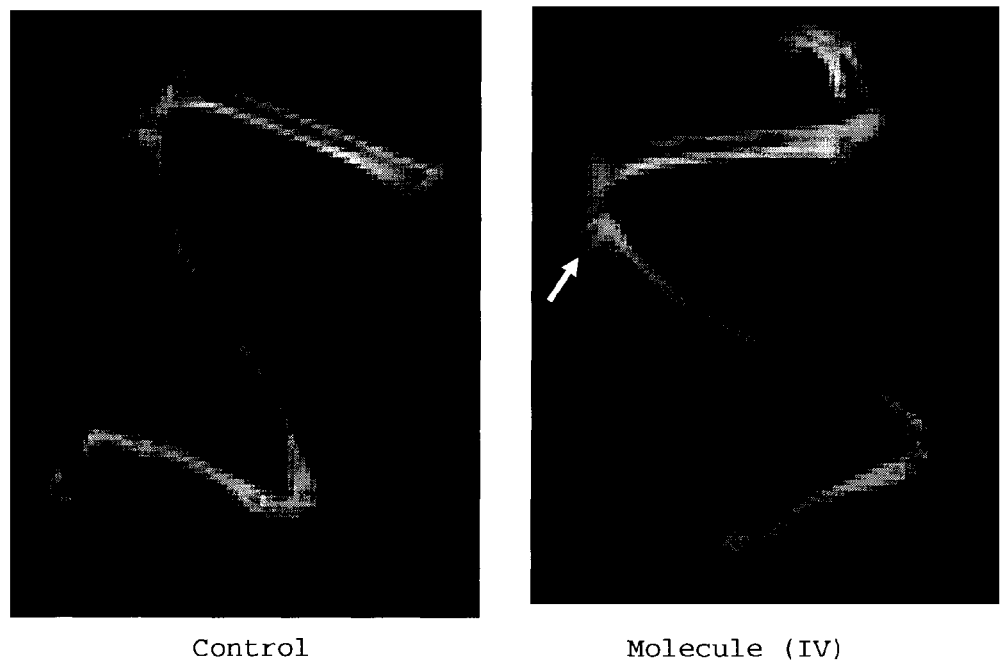
FIG. 3 shows radiographs of untreated (control) or treated mice with the molecule (IV) demonstrating an inhibitory effect of bone degradation characterized by the increase in the bone mineral density in the epiphyseal area (white arrow). This effect demonstrates tropism of the molecule (IV) for the bone mineral fraction.

The obtained results demonstrate that the complete injected compound was actually bound to the bone tissue by increasing bone apposition considering the radiographic images (see FIG. 3) and simultaneously induced a reduction in the tumoral volume (extra-osteal site) by releasing the anti-tumoral domain (see FIG. 4), similar results being obtained for both concentrations (−20/−30% of reduction of the tumoral volume).

2.2. Molecules with Strong Bone Tropism

This study was conducted by using the following molecule 4, illustrating a <<simplified molecule>> of the invention:

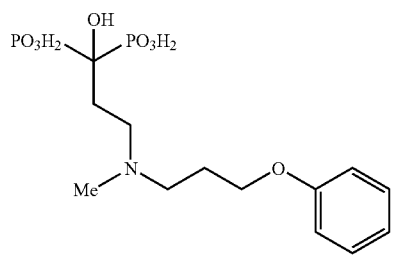

4

In Vivo Test:

2-3 week old young mice (Swiss strain) were treated with the molecule 4 or with a disodium salt of zoledronic acid (diluted in PBS) sub-cutaneously twice a week, at the concentration of 0.35 μmol/kg.

The disodium salt of zoledronic acid is a third generation bisphosphonate which is used here as a comparison molecule.

Figure 2:
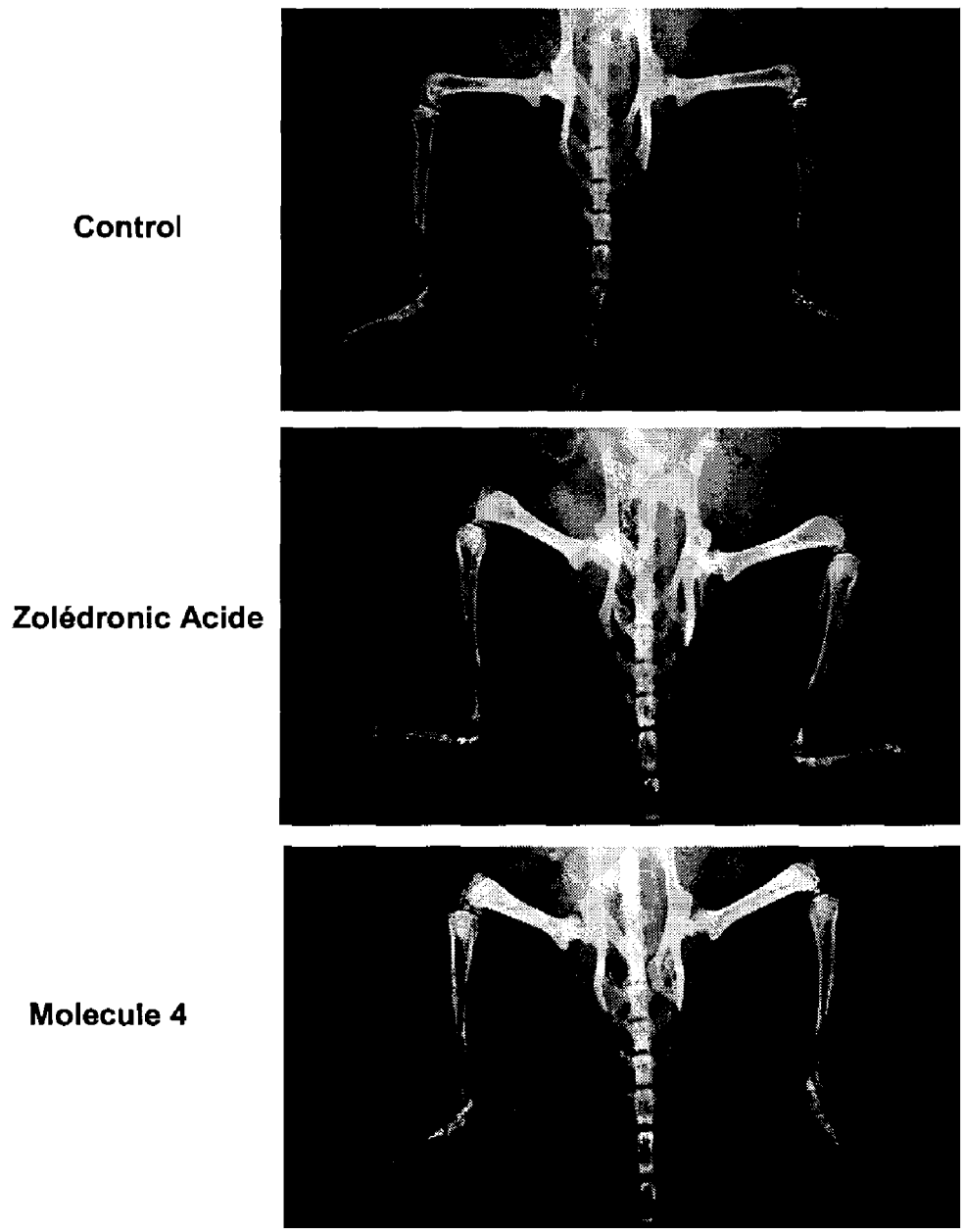
FIG. 2 shows radiographs of untreated (control) or treated mice with the molecule 4 or the disodium salt of zoledronic acid, after 4 weeks of treatment.

After 4 weeks of treatment, it is seen that there is no incidence on the weight follow-up, nor on the general condition of the mice treated with one of these two molecules. The radiographs shown in FIG. 2 reveal an increase in the mineral density after 4 weeks of treatment with the disodium salt of zoledronic acid or with the molecule 4 as compared with <<control>> mice. Further, the measured specific bone volume (BV/TV=volume of the bone based on the total volume of analyzed tissue) is shown in the following table in the case of administration of the molecule 4 or of the disodium salt of zoledronic acid according to the procedure described above or in the case of absence of treatment (control value).

|  | femur | BV/TV | average |
|---|---|---|---|
| Control | left | 56.58% | 62.89% |
|  | right | 69.20% |  |
| Disodium salt of zoledronic acid | left | 72.72% | 74.02% |
|  | right | 75.33% |  |
| Molecule 4 | left | 73.69% | 73.88% |
|  | right | 74.08% |  |

These results show that the molecule 4 is capable of inducing an increase in the total specific bone volume of femurs in mice treated with this molecule, comparable with the values obtained with the disodium salt of zoledronic acid, a reference product.

2.3. Fluorescent Molecules

The molecule (II) was tested in vitro on different cell lines and did not have any cytotoxic activity. Administration in mice did not either reveal any cytotoxic activity.

The molecule (II) has the property of absorbing light energy (excitation wavelength λ: 280 nm) and of rapidly releasing it as fluorescent light. Thus, the emission spectrum of the molecule (II), after excitation at 280 nm, reveals that this molecule re-emits light at a wavelength of 500 nm.

The invention claimed is:

1. A hydroxy-bisphosphonic acid derivative fitting the general formula (I):

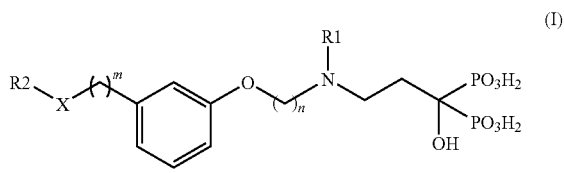

wherein:
n and m designate, independently of each other, an integer varying from 1 to 4,
X designates an oxygen atom or an N—R3 group,
R1 and R3 designate, independently of each other, a linear or branched $C_1$-$C_6$ alkyl group and
R2 designates a residue of a molecule of therapeutic or diagnostic interest,
or a pharmaceutically acceptable salt thereof.

2. The hydroxy-bisphosphonic acid derivative according to claim 1, wherein R2 is a residue of a fluorescent molecule or a luminescent molecule.

3. The hydroxy-bisphosphonic acid derivative according to claim 1, wherein R2 is a residue of a useful active ingredient for treatment or diagnosis of a pathology of osteolytic or osteocondensing bone remodeling.

4. The hydroxy-bisphosphonic acid derivative according to claim 1, wherein R2 is a residue of an active ingredient selected from standard chemotherapy agents, anti-inflammatory agents, and peptides with bone pro-formation or anti-resorption activity.

5. The hydroxy-bisphosphonic acid derivative according to claim 1, wherein it is selected from the following compounds:

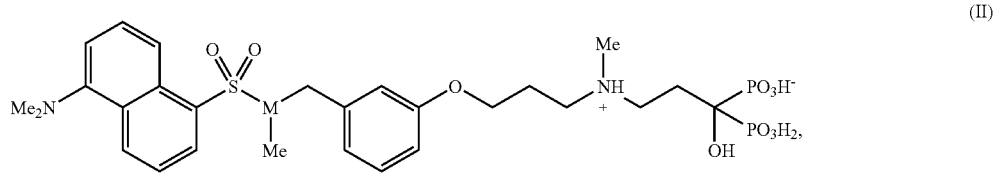

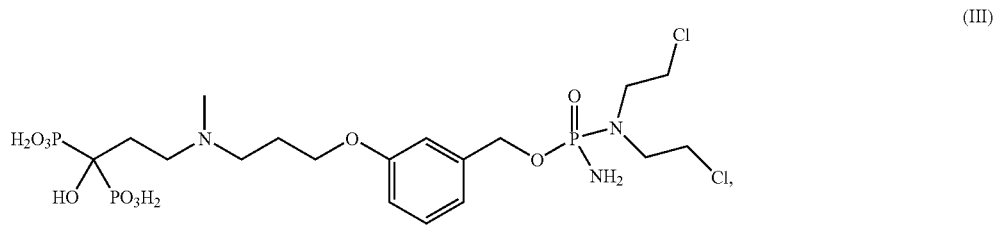

-continued

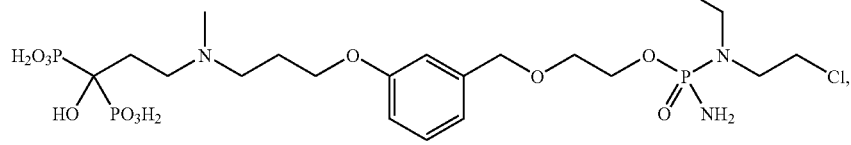
(IV)

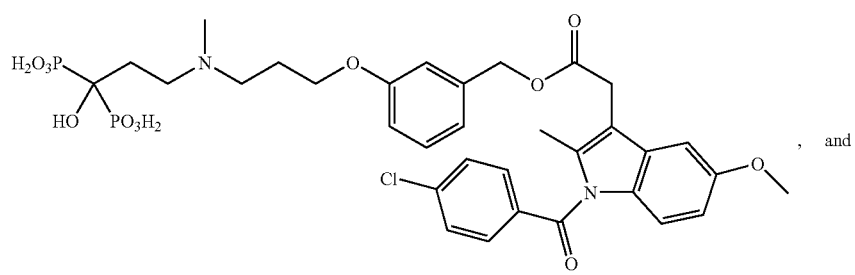
(V)
, and

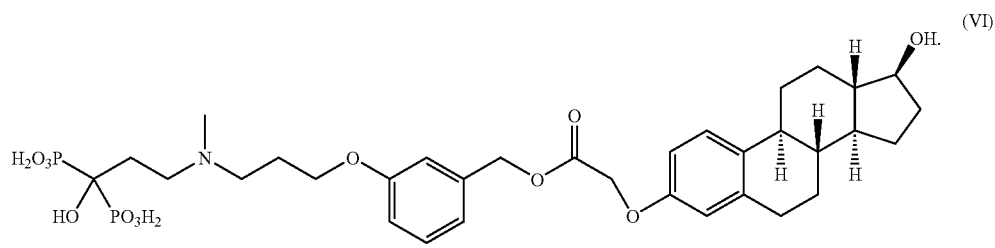
(VI)

6. A pharmaceutical or diagnostic composition comprising at least one hydroxy-bisphosphonic acid derivative according to claim 1 or a pharmaceutically acceptable salt thereof and at least one pharmaceutically acceptable carrier.

7. The pharmaceutical or diagnostic composition according to claim 6, wherein it appears as an injectable solution or as a patch.

8. The hydroxy-bisphosphonic acid derivative according to claim 2, wherein the residue of the fluorescent molecule is the (5-dimethylamino)naphthalene-1-sulfonyl residue, the 7-nitro-1,2,3-benzoxadiazole residue or fluorescein and the luminescent molecule is dioxetane derivatives.

9. The hydroxy-bisphosphonic acid derivative according to claim 3, wherein the pathology of osteolytic or osteocondensing bone remodeling is chosen from among primitive bone tumors, bone metastases, multiple myeloma, deregulations of the phospho-calcium metabolism, osteoporosis, and inflammatory pathologies.

10. The hydroxy-bisphosphonic acid derivative according to claim 9, wherein the primitive bone tumor is chosen from among an osteosarcoma, a chondrosarcoma, a giant cell tumor and Ewing's sarcoma; the deregulation of the phospho-calcium metabolism is hypercalcemia; and the inflammatory pathology is chosen from among rheumatoid arthritis and peri-prosthetic loosenings.

11. The hydroxy-bisphosphonic acid derivative according to claim 4, wherein the standard chemotherapy agent is chosen from among ifosfamide, derivatives of cis-platinum and doxorubicin; the anti-inflammatory agent is chosen from among cortico-steroids and non-steroidal anti-inflammatory agents.

12. The hydroxy-bisphosphonic acid derivative according to claim 11, wherein the cortico-steroid is dexamethasone and the non-steroidal anti-inflammatory agent is ibuprofen.

13. A method for preparing a compound of formula (I) according to claim 1 or one of its pharmaceutically acceptable salts, comprising the following successive steps:

(a) coupling between a compound of the following formula (A):

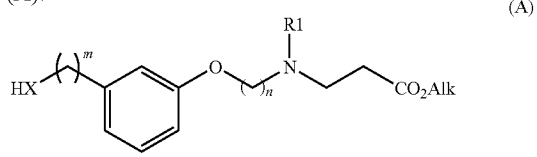
(A)

for which R1, X, n and m are as defined in claim 1 and Alk represents a linear or branched $C_1$-$C_6$ alkyl group,
and the molecule of therapeutic or diagnostic interest corresponding to the residue R2 as defined in claim 1,
in order to obtain a compound of the following formula (B):

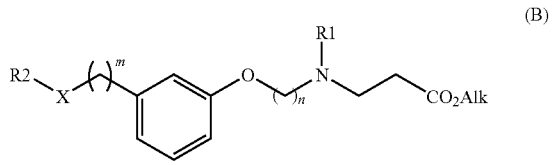
(B)

for which R1, R2, X, n and m are as defined in claim 1, and Alk is as defined above, (b) saponification of the terminal ester of the compound of formula (B) obtained in the previous step (a) in order to obtain a compound of the following formula (C):

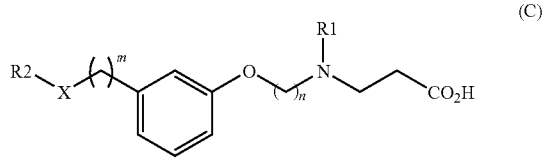

(C)

for which R1, R2, X, n and m are as defined in claim 1, (c) conversion of the free carboxylic acid function of the compound of formula (C) obtained in the previous step into a hydroxy-bisphosphonic function in order to obtain the compound of formula (I), (d) optionally salification of the compound of formula (I) obtained in the previous step (c) for obtaining a pharmaceutically acceptable salt of the latter, and (e) separation from the reaction medium of the compound of formula (I) or of one of its pharmaceutically acceptable salts obtained in the previous step (c) or (d).

14. The method according to claim 13, wherein Alk represents a tert-butyl group.

* * * * *

UNITED STATES PATENT AND TRADEMARK OFFICE
CERTIFICATE OF CORRECTION

PATENT NO. : 8,361,993 B2
APPLICATION NO. : 12/811602
DATED : January 29, 2013
INVENTOR(S) : Maxim Egorov et al.

It is certified that error appears in the above-identified patent and that said Letters Patent is hereby corrected as shown below:

On the Title Page of the Patent

Item (73) Assignees should read as:
--Universite de Nantes, Nantes (FR); Chu Nantes, Nantes (FR); Institut National de la Santa et de la Recherche Medicale (INSERM), Paris (FR); Centre National de la Recherche Scientifique (CNRS), Paris (FR)--.

Signed and Sealed this
Second Day of April, 2013

Teresa Stanek Rea
*Acting Director of the United States Patent and Trademark Office*